United States Patent [19]

Hermecz et al.

[11] 4,220,771
[45] Sep. 2, 1980

[54] 2,3-POLYMETHYLENE-4-OXO-4H-PYRIDO[1,2-A]PYRIMIDINES

[75] Inventors: István Hermecz, Budapest; Ferenc Fülöp, Szeged; Zoltán Mészáros, Budapest; Gábor Bernáth, Szeged; József Knoll, Budapest, all of Hungary

[73] Assignee: Chinoin Gyogyszer és Vegyészeti Termékek Gyára Rt, Budapest, Hungary

[21] Appl. No.: 935,071

[22] Filed: Aug. 18, 1978

[30] Foreign Application Priority Data

Aug. 19, 1977 [HU] Hungary .................. CI 1766

[51] Int. Cl.² .............. C07D 487/14; A61K 31/505
[52] U.S. Cl. .................................. 544/252; 424/251
[58] Field of Search .......................... 544/252; 424/251

[56] References Cited

U.S. PATENT DOCUMENTS

| 2,992,221 | 7/1961 | Peterson et al. ............ 544/252 X |
| 3,271,396 | 9/1966 | Bernstein et al. ............ 544/252 |
| 3,790,573 | 2/1974 | Blackburn et al. ............ 424/251 X |
| 3,965,100 | 6/1976 | Yale ............................... 544/252 |
| 4,033,961 | 7/1977 | Schwender et al. .......... 544/247 |
| 4,083,980 | 4/1978 | Schromm et al. ............ 424/251 |

OTHER PUBLICATIONS

Moehrle, et al., Chemical Abstracts, vol. 80, 14889k (1974).
Devi, et al., Chemical Abstracts, vol. 85, 160393p (1976).
Noda, et al., Chemical Abstracts, vol. 88, 6929y (1978).
Brown, et al., Chemical Abstracts, vol. 75, 48839f (1971).

*Primary Examiner*—Donald G. Daus
*Assistant Examiner*—Diana G. Rivers
*Attorney, Agent, or Firm*—Karl F. Ross

[57] ABSTRACT

Pharmaceutical intermediates, morphine potentiators and other compounds have the formula

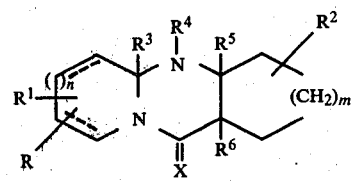

wherein R is hydrogen, halogen, $C_{1-4}$ alkyl, hydroxy, nitro, amino, carboxy or a carboxylic acid derivate radical, $R^1$ is hydrogen or a $C_{1-4}$ alkyl, $R^2$ is hydrogen or $C_{1-4}$ alkyl, $R^3$ is hydrogen, $R^4$ is hydrogen or $C_{1-4}$ alkyl, $R^5$ is hydrogen $R^6$ is hydrogen or $R^3$ and $R^4$ and/or $R^5$ and $R^6$ form a chemical bond, X is oxygen or imino, m is 1, 2, 3 or 4, n is 0, 1, 2 or 3, and if n is 1, then the dotted lines can stand for bonds, with the proviso that if m=1 and n=1 and if in the 2,3-, 6,7-, 8,9- and 1,10-positions double bonds are present, and $R^1$ and $R^2$ are hydrogen, then R is other than 9-hydroxy or 9-methyl; if m=2 and n=1 and $R^2$ is hydrogen, then at least one of R and $R^1$ is other than hydrogen; and if m=2 and n=2 and $R^2$ is hydrogen and the molecule is a 2,3,4,6,7,8,9,10-octahydro derivative, then at least one of R and $R^1$ is other than hydrogen or an acid-addition or quaternary salt thereof.

9 Claims, No Drawings

2,3-POLYMETHYLENE-4-OXO-4H-PYRIDO[1,2-A]PYRIMIDINES

The present invention relates to tricyclic nitrogen bridge-head compounds, acid-addition salts and quaternary salts thereof and to a process for the preparation of the above compounds.

The preparation of only a few similar compounds has been reported in the prior art. Thus, for example, 2-aminopyridine and 2-ethoxycarbonyl-cyclohexanone were reacted in polyphosphoric acid ethyl ester at 165° C. and after chromatographing on an alumina column 2,3-tetramethylene-4-oxo-4H-pyrido(1,2-a)pyrimidine was prepared with a yield of 50% (J. Chem. Soc. C 1971, 2163). 2,3-Tetramethylene-4-oxo-6,7,8,9-tetrahydro-4-H-pyrido(1,2-a)-pyrimidine was prepared with a 78% yield from an inner salt of 11-oxo-1,2,3,4,5,7,8,9,10,11-decahydro-pyrido-(1,2-b)cinnoline-6-ium hydroxide in a Photoisomerization reaction lasting 5 days. The same compound was prepared with only a 14% yield by heating 2-imino-piperidine hydrochloride and 2-ethoxycarbonyl-cyclohexanone under nitrogen atmosphere in acetic acid in a reaction lasting 20 hours (J. Org. Chem. 40, 2201, 1975). Recently, 2-amino-pyridine, and some derivatives theeof substituted in the 3-position have been reacted with 2-ethoxycarbonyl-cyclopentanone optionally in the presence of an inert solvent. As a catalyst concentrated sulfuric acid, methane sulfonic acid, p-toluene sulfonic acid or an ion-exchanger resin in acid phase may be used in the reaction. This method results in 50–68% of 2,3-trimethylene-4-oxo-4H-pyrido-(1,2-a)pyrimidine derivatives, patented as tranquillizers and as antianxiolythic compounds (U.S. Pat. No. 3,965,100).

2-Amino-cyclohexane-carboxylic acid and 2-methoxy-4,5,6,7-tetrahydro-3H-azepine were reported to react with each other in acetone for 2 hours to produce 2,3-tetramethylene-4-oxo-2,3,4,6,7,8,9,10-octahydro-pyrido(1,2-a)-azepine, melting at 100° C. (U.S. Pat. No. 2,992,221 and GFR Pat. No. 1,088,968).

The invention is based partly on the recognition that the ring closure may be carried out with a good yield in the presence of phosphoric acid under acidic conditions or in the presence of aromatic tertiary amines under basic conditions with the elimination of the chromatographic step and partly that the new compounds exhibit an analgesic and morphine-potentiating activity and may be used as a therapeutically active analgesic pharmaceutical compositions.

The invention relates to new compounds of the formula I and acid-addition salts and quaternary salts thereof—wherein R is hydrogen or halogen, $C_{1-4}$ alkyl, hydroxy, nitro, amino, carboxy, or a carboxylic acid derivative radical, $R^1$ is hydrogen or $C_{1-4}$ alkyl, $R^2$ is hydrogen or $C_{1-4}$ alkyl, $R^3$ is hydrogen, $R^4$ is hydrogen or $C_{1-4}$ alkyl, $R^5$ is hydrogen, $R^6$ is hydrogen or $R^3$ and $R^4$ and/or $R^5$ and $R^6$ form a chemical bond, X is oxygen or imino, m is 1, 2, 3 or 4, n is 0, 1, 2 or 3 and if n is 1, then the dotted lines can be bonds, with the proviso that if m=1 and n=1 and if in the 2,3-, 6,7-8,9- and 1,10-positions double bonds are present and and $R^1$ and $R^2$ are hydrogen, then R is other than 9-hydroxy or 9-methyl and if m=2 and n=1 and $R^2$ is hydrogen, then at least one of R and $R^1$ is different from hydrogen and if m=2 and n=2 and $R^2$ is hydrogen and the molecule is a 2,3,4,6,7,8,9,10-octahydro-derivative then at least one of R and $R^1$ is other than hydrogen.

The term "$C_{1-4}$ alkyl" as used hereinafter means straight or branched $C_{1-4}$ alkyl, such as methyl, ethyl, n-propyl, isopropyl, n-butyl, isobutyl. The term "halogen" means chlorine, bromine, iodine or fluorine. The term "carhoxylic acid derivative radical" means carboxylic acid esters (such as alkyl, aryl, or aralkyl esters, preferably alkoxycarbonyl, phenyloxycarbonyl, or benzyloxycarbonyl), acid amides (such as carbamoyl or N-alkyl or N,N-dialkylcarbamoyl), acid azides, acid hydrazides or nitriles.

Preferred are those compounds of the formula I wherein

R is hydrogen, methyl, ethyl, chlorine, bromine, nitro, amino, carboxy, methoxy carbonyl, ethoxycarbonyl or carbamoyl, $R^1$ is hydrogen or methyl, $R^2$ is hydrogen, methyl, ethyl or tertiary butyl, $R^3$, $R^4$, $R^5$ and $R^6$ are hydrogen or $R^3$ and $R^4$ and/or $R^5$ and $R^6$ together form a chemical bond, X is oxygen, and n=0, 1 or 2 and m is 1 to 4, and the acid-addition and quaternary salts thereof.

Particularly preferred are the following compounds of the formula I 7-methyl-2,3-trimethylene-4-oxo-4H-pyrido(1,2-a)pyrimidine and acid-addition salts and quaternary salts thereof, 8-methyl-2,3-trimethylene-4-oxo-4H-pyrido(1,2-a)pyrimidine, acid-addition salts and quaternary salts thereof, 6,8-dimethyl-2,3-trimethylene-4-oxo-4H-pyrido(1,2-a)-pyrimidine and acid-addition salts and quaternary salts thereof, 6-methyl-2,3-tetramethylene-4-oxo-4H-pyrido(1,2-a)pyrimidine, salts and quaternary salts thereof, 2,3-pentamethylene-4-oxo-4-H-pyrido(1,2-a)pyrimidine, acid-addition salts and quaternary acid-addition salts thereof, 2,3-hexamethylene-4-oxo-4H-pyrido(1,2-a)pyrimidine, acid-addition salts and quaternary salts thereof.

The invention further relates to a process for the preparation of tricyclic nitrogen bridge-head compounds of the formula I

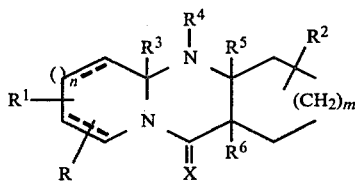 (I)

salts and quaternary salts thereof—wherein

R is hydrogen or halogen, $C_{1-4}$ alkyl, hydroxy, nitro, amino, carboxy or a carboxylic acid derivative radical, $R^1$ is hydrogen or $C_{1-4}$ alkyl, $R^2$ is hydrogen or $C_{1-4}$ alkyl, $R^3$ is hydrogen, $R^4$ is hydrogen or $C_{1-4}$ alkyl, $R^5$ is hydrogen, $R^6$ is hydrogen or $R^3$ and $R^4$ and/or $R^5$ and $R^6$ can form together a chemical bond X is oxygen or imino, m is 1, 2, 3 or 4, n is 0, 1, 2, or 3 and if n is 1, the dotted lines stand for a double bond, comprising (a) reacting a 2-amino-pyridine derivative of the formula II

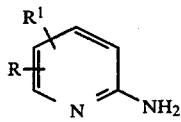 (II)

or an acid-addition salt thereof with a cyclic oxo compound of the formula III

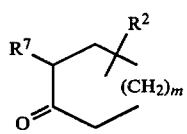 (III)

wherein $R^7$ is alkoxycarbonyl containing $C_{1-4}$ alkyl, a carboxylic acid radical, carboxamido or nitrile and if
2,3-trimethylene-9-methyl-4-oxo-4H-pyrido(1,2-a)pyrimidine,
2,3-trimethylene-9-hydroxy-4-oxo-4H-pyrido(1,2-a)pyrimidine,
2,3-trimethylene-4-oxo-6,7,8,9-tetrahydro-4H-pyrido-(1,2-a)pyrimidine, or
2,3-tetramethylene-4-oxo-2,3,4,6,7,8,9,10-octahydropyrido(1,2-a)azepine - is prepared, the reaction is carried out in the presence of phosphoric acid or an aromatic tertiary amine, or (b) condensing an amine of the formula IV

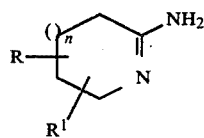 (IV)

with a cyclic oxo compound of the formula III, in an inert solvent, optionally in the presence of phosphoric acid, or (c) condensing an imino ether of the formula V

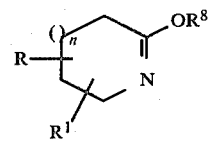 (V)

wherein $R^8$ is $C_{1-4}$ alkyl with an amine of the formula VI

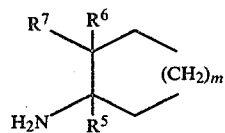 (VI)

in an inert solvent, in the presence of phosphoric acid, and reducing, if desired the obtained compound of the formula I—wherein the dotted lines are an optional bonds and $R^3$ and $R^4$ and/or $R^5$ and $R^6$ form a chemical bond—in order to reduce the double bonds in the regions of the dotted lines and/or the double bonds formed between $R^3$-$R^4$ and/or $R^5$-$R^6$, and converting, if desired the obtained compound of the formula I to an acid addition or quaternary salt and/or reducing the obtained quaternary salt and/or setting free a compound of the formula I from its salt and converting, if desired, the obtained compound of the formula I to another compound of the formula I.

According to an embodiment of the step (a) of the invention 2-amino-pyridine derivatives of the formula II or an acid-addition salt thereof are reacted with a cyclic oxo compound of the formula III wherein $R^7$ is alkoxycarbonyl containing $C_{1-4}$ alkyl, carboxylic acid, carboxamido or nitrile - obtaining nitrogen bridgehead compounds of the formula I wherein n is 1, the dotted lines are double bonds, and $R^3$ and $R^4$ and/or $R^5$ and $R^6$ form a chemical bond.

2-amino-pyridine of the formula II or an acid-addition salt thereof is condensed with a cyclic oxo compound of the formula III, preferably in the presence of phosphoric acid. The condensation may, however, also be carried out by reacting the acid addition salt of 2-amino-pyridine of the formula II with the cyclic oxo compound of the formula III in the presence of an aromatic tertiary amine. In step (b) a compound of the formula IV is condensed with a cyclic oxo-compound of the general formula III by heating the mixture in an inert solvent, if desired, in the presence of an acid condensing agent, preferably phosphoric acid or polyphosphoric acid. Thus nitrogen bridgehead compounds of the formula I are obtained wherein $R^3$ and $R^4$, $R^5$ and $R^6$ form a chemical bond. In step (c) of the method, an imino ehter of the formula V wherein $R^8$ is $C_{1-4}$ alkyl is condensed with an amine of the formula VI - with heating of the mixture in an inert solvent, if desired in the presence of an acid condensing agent, preferably phosphoric acid or polyphosphoric acid. Thus nitrogen bridgehead compounds of the formula I are obtained wherein $R^3$ and $R^4$ form a chemical bond.

The pyrido (1,2-a)pyrimidine compound of the formula I obtained by any of steps (a), (b) and (c) -wherein at least the dotted lines are parts of double bonds, or $R^3$ and $R^4$ and/or $R^5$ and $R^6$ form a chemical bond - is reduced if desired, by a complex metal hydride or catalytically activated hydrogen.

The obtained nitrogen bridgehead compound of the formula I can be converted, if desired, to an acid-addition or quaternary salt, or may be set free from the acid-addition salt, or the quaternary salt may be reduced.

When condensing 2-amino-pyridine of the formula II or an acid-addition salt thereof with a cyclic oxo compound of the formula III as phosphoric acid, preferably polyphosphoric acid can be used. The reaction mixture may be further processed by diluting the reaction mixture with water and neutralizing it with a 10% by W/V alkaline solution, preferably sodium hydroxide under cooling. The precipitated crystals can be filtered or centrifuged to recover the crystals. The condensation can also be carried out by using phosphorus trichloride oxide as solvent and thus the necessary amount of the polyphosphoric acid may be reduced. When further processing the reaction mixture it is decomposed with alcohol and the hydrochloride salt precipitates from the cooled reaction mixture in the form of crystals, which may be recovered by filtration. The reaction mixture may also be decomposed with an aqueous alkaline solution when carrying out the ring closure in the presence of phosphorus trichloride oxide. In this case the ring-closed compound is obtained in the form of a base. The ring closure can be carried out at 20° to 250° C., preferably at 80° to 160° C.

Condensation of the hydrohaloide of 2-amino-pyridine of the formula II with a cyclic oxo compound of the formula III is preferably carried out in the presence of an aromatic tertiary nitrogen-containing base. As aromatic tertiary nitrogen-containing bases pyridine, picoline, quinoline, luthidine etc. are preferably employed. The reaction is preferably carried out at the boiling point of the solvent used. The reaction mixture is evaporated at reduced pressure and crystallized from alcohol. Thus hydrohalides are obtained.

The base is, if desired, set free from the hydrohaloides by methods known per se.

As inert solvents in the method steps (b) and (c) alcohols (preferably methanol or ethanol), aromatic hydrocarbons (benzene, toluene, xylene), halogenated hydrocarbons (chloroform, dichloromethane, chlorobenzene, carbon-tetrachloride), ketones (acetone, ethyl-methyl-ketone), esters (such as ethyl acetate) may be used. The reaction is preferably carried out at the boiling point of the inert solvent. The residue after evaporation is crystallized from a suitable solvent or solvent mixture. The reaction may also be performed in the presence of an acid condensing agent. As acid condensing agents phosphoric acid, preferably polyphosphoric acid may be employed. The reaction is performed at 20° to 250° C., preferably at 80° to 160° C. The reaction mixture is further processed by diluting with water, followed by neutralization with an alkaline solution, preferably with 10% by W/V sodium hydroxide solution. The precipitated crystals may be removed by filtration.

If R is nitro in the tricyclic nitrogen bridgehead compounds of the formula I, then the reaction may be carried out in aqueous medium with metallic iron under the circumstances of the Béchamp reduction and thus the nitro group is reduced to an amino group.

Palladium and Raney nickel or platina, platinaoxide may preferably be used as catalysts during the catalytic hydrogenation, which is preferably carried out at 0° to 50° C., at atmospheric to 10 atm. overpressure in the presence of an inert solvent.

As inert solvents preferably alcohols may be employed. The reduced product may be recovered after removing the catalyst by filtration, followed by evaporation of the obtained solution. When performing the reduction with complex metal hydrides, preferably sodiumborohydride, sodiumcyanoborohydride, sodium-bis(2-methoxy-ethoxy) aluminum hydride or, lithiumaluminum hydride may be used. As a solvent water, alcohol, benzene, ether or, tetrahydrofuran may be employed depending on the complex metal hydride used.

The reduction may preferably be carried out at 0° to 50° C. The reduced product is recovered by removing the solvent by distillation or if water is used, by shaking out with a water-immiscible organic solvent (chloroform, benzene, ethyl acetate) and by evaporation of the organic solvent.

In the quaternizing reaction the usually employed quaternizing agents, such as alkyl halides (ethyl iodide, methyl bromide, methyl chloride), aralkyl halides (benzyl chloride), alkyl sulfates (dimethyl sulfate, diethyl sulfate), benzene sulfonates and alkylated derivatives thereof (benzene sulfonic acid methyl ester, p-toluenesulfonic acid ethyl ester), alkyl phosphates (trimethyl phosphate, triethyl phosphate), tetraalkyloxonium fluoroborate etc. may be employed. The reaction may be performed in an excess of the quaternizing agent or an inert solvent at a temperature of 0° to 200° C. As an inert solvent apolar aromatic hydrocarbons, such as benzene or toluene, halogenated hydrocarbons (chloroform, chlorobenzene), ethers (dioxan), or aprotic dipolar solvents, dimethylformamide or nitriles (acetonitrile), nitrated hydrocarbons (nitromethane, nitrobenzene), ketones (acetone, ethyl-methyl-ketone), hexamethyl-phosphortriamide or solvent mixtures are preferred.

In the quaternizing reaction the formed quaternary salt precipitates from the reaction mixture and may be removed, for example by filtration.

From the nitrogen bridgehead comounds of the formula I, acid-addition salts may be formed with pharmaceutically accepted organic acids or inorganic acids by methods known per se. Thus hydrohalides, such as hydrochlorides, hydrobromides, hydroiodides, salts of sulfuric acid, phosphoric acid, perchloric acid, formic acid, acetic acid, citric acid, maleic acid etc., are preferably prepared.

An obtained compound of the formula I, may be converted, if desired, to another compound of the formula I by methods known per se. Thus, for example, a compound of the formula I containing carboxy as R may be converted to a compound of the formula I, wherein R is hydrogen and the corresponding esters or amides may be obtained by esterification or amidation. The invention also includes these additional conversions.

Compounds of the formulae II, III, IV, V or VI may be prepared from commercially available compounds by methods known per se or the compounds themselves are commercially available.

The invention also includes the possible stereo isomers of nitrogen bridgehead compounds of the formula I.

The prepared compounds can be useful as active ingredients of pharmaceutical compositions or as intermediate products in the synthesis of biologically active compounds.

Compounds of the invention have antiinflammatory, analgesic, antipyretic activity, or other favorable activity upon the central nervous system (such as sedative, hypnotic, tranquillizer activity; other compounds have PG-antagonistic, thrombocyte aggregation inhibiting, anti-asthmatic activity, favorable circulation and antiarteriosclerotic activity.

Some representatives of the compounds of the invention have significant antibacterial and antimicrobial activity.

Some of the derivatives have particularly significant analgesic and morphine-potentiating activity. The corresponding test results are to be found in Table 1.

In testing for toxicity the mice were observed for 48 hours after administration of the compounds, whereafter the $LD_{50}$ values were determined by the Litchfield-Wilcoxon graphic method. Also the analgesic and morphine-potentiating activities were investigated on mice. The test results obtained in a "hot plate" test (J. Pharm. Exp. Therp. 80 130 (1944) and Kiserl. Orvostudomany 2, 295 (1950) and results obtained in laparotomic test of Knoll (Animal and Clinical Pharmacologic Techniques in Drug Evaluation. Vol. 2. 305-321 (1967), Year Book Publ. Chicago) are shown in Table 1.

Table 1

| Compound | $LD_{50}$ mg./kg. i.v. | $LD_{50}$ mg./kg. s.c. | Hot plate $ED_{50}$ mg./kg. i.v. | Hot plate $ED_{50}$ mg./kg. s.c. | Dose potentiating the activity of 5 mg. morphine $ED_{50}$ mg./kg. i.v. |
|---|---|---|---|---|---|
| 7-Methyl-2,3-trimethylene-4-oxo-4H-pyrido(1,2-a)-pyrimidine hydrochloride | 120 | — | 47 | — | 1.0 |
| 8-methyl-2,3-trimethylene-4-oxo-4H-pyrido(1,2-a)-pyrimidine hydrochloride | 120 | — | 65 | — | 4.8 |
| 6,8-dimethyl-2,3-trimethylene-4-oxo-4H-pyrido-(1,2-a)pyrimidine hydrochloride | 120 | — | 42 | — | 1.0 |
| 6-methyl-2,3-tetramethylene-4-oxo-4H-pyrido(1,2-a)-pyrimidine hydrochloride | 160 | — | — | — | 7.8 |
| 2,3-pentamethylene-4-oxo-4H-pyrido-(1,2-a)pyrimidine-hydrochloride | 210 | 630 | — | 66 | 3.7 |
| 2,3-hexamethylene-4-oxo-4H-pyrido-(1,2-a)pyrimidine hydrochloride | 125 | 500 | — | 105 | 4.5 |
| PROBON | 220 | 790 | 43 | 75 | 25.0 |

As the reference compound the analgesic PROBON® used and the corresponding data therefor are also given in the Table. The outstanding morphine-potentiating activity of the compounds can be seen from the data of the Table. The compounds similarly potentiate the analgesics of the morphine type and other major analgetica, and thus their therapeutic dose may be reduced to a great extent whereby the detrimental side effects are also reduced.

The nitrogen bridgehead tricyclic compounds of the formula I can be used as active ingredients in compositions containing inert, nontoxic solid or liquid diluents or carriers. The compositions may be used in solid (tablets, capsules, dragée etc.) or liquid (such as solution, suspension, emulsion) form.

As carriers, the usual substances such as talcum, calcium carbonate, magnesium stearate, water, polyethylene glycolate etc. may be used. The compositions may contain, if desired, usual additives, such as disintegrating agents, emulsifying agents as well.

Tricyclic nitrogen bridgehead compounds of the formula I may be combined in the compositions mentioned above with other analgesic compounds such as morphine derivatives (morphine, azidomorphine, azidocodeine), morphinine derivatives, benzomorphane compounds (phenazocine, pentazocine), phenylpiperidine derivatives (petidine, nisentile). The latter derivatives may be used in a smaller dose due to the synergistic activity upon combination with the compounds of the invention and thus the unfavorable side effects (tolerance, dependency, breath depression) practically need not be considered.

Further details of the invention are illustrated in the following Examples.

EXAMPLES 1 TO 20

20 mmoles of 2-ethoxycarbonyl-1-oxo-cycloalkane (see Table 2) and 20 mmoles of 2-amino-pyridine are stirred together in 20 g. of polyphosphoric acid for 90 minutes at 100° C. The reaction mixture is diluted with 20 ml. of water and after cooling the pH-value of the mixture is adjusted to 7 by adding 10% by W/V of sodium hydroxide solution. The precipitated crystals are filtered, washed with a small amount of water and dried. The obtained nitrogen bridgehead compound is recrystallized from the given solvent. The obtained compounds and their constants are summarized in Table 2.

Table 2

| Example | Starting material 2-ethoxycarbonyl-1-oxo-cycloalkane | Starting material 2-amino-pyridine | Product | Yield % | Mp. °C. | Recrystallization solvent | Empirical formula | Analysis Calculated / Found C % | H % | N % |
|---|---|---|---|---|---|---|---|---|---|---|
| 1 | 2-ethoxycarbonyl-1-oxo-cyclopentane | 2-amino-pyridine | 2,3-trimethylene-4-oxo-4H-pyrido-(1,2-a)pyrimidine | 66 | 151-152 | diisopropyl-ether | $C_{11}H_{10}N_2O$ | 70.95 / 70.78 | 5.41 / 5.67 | 15.05 / 15.26 |
| 2 | 2-ethoxycarbonyl-1-oxo-cyclopentane | 2-amino-6-methyl-pyridine | 2,3-trimethylene-6-methyl-4-oxo-4H-pyrido(1,2-a) | 84 | 160-161 | ethanol | $C_{12}H_{12}N_2O$ | 71.98 / 71.75 | 6.04 / 6.27 | 13.99 / 14.37 |

Table 2-continued

| Example | Starting material 2-ethoxycar-bonyl-1-oxo-cycloalkane | 2-amino-pyridine | Product | Yield % | Mp. °C. | Recrystallization solvent | Empirical formula | Analysis Calculated Found C % | H % | N % |
|---|---|---|---|---|---|---|---|---|---|---|
| 3[x] | 2-ethoxycar-bonyl-1-oxo-cyclopentane | 2-amino-5-methyl-pyridine | pyrimidine 2,3-trimethylene-7-methyl-4-oxo-4H-pyrido(1,2-a)-pyrimidine | 72 | 145–146 | ethanol | $C_{12}H_{12}N_2O$ | 71.98 71.70 | 6.04 6.25 | 13.99 13.72 |
| 4 | 2-ethoxycar-bonyl-1-oxo-cyclopentane | 2-amino-4-methyl-pyridine | 2,3-trimethylene-8-methyl-4-oxo-4H-pyrido(1,2-a)-pyrimidine | 84 | 168–169 | ethyl-acetate | $C_{12}H_{12}N_2O$ | 71.98 72.04 | 6.04 6.03 | 13.99 13.76 |
| 5[+] | 2-ethoxycar-bonyl-1-oxo-cyclopentane | 2-amino-3-methyl-pyridine | 2,3-trimethylene-9-methyl-4-oxo-4H-pyrido(1,2-a)pyrimidine | 81 | 109 | ethanol | $C_{12}H_{12}N_2O$ | 71.98 71.79 | 6.04 6.12 | 13.99 13.78 |
| 6 | 2-ethoxycar-bonyl-1-oxo-cyclopentane | 2-amino-4,6-di-methyl-pyridine | 2,3-trimethylene-6,8-dimethyl-4-oxo-4H-pyrido-(1,2-a)pyrimidine | 81 | 163–164 | ethanol | $C_{13}H_{14}N_2O$ | 72.86 72.90 | 6.59 6.59 | 13.08 12.76 |
| 6 | 2-ethoxycar-bonyl-1-oxo-cyclopentane | 2-amino-5-pyri-dine | 2,3-trimethylene-7-chloro-4-oxo-4H-pyrido(1,2-a)-pyrimidine | 82 | 151–152 | ethanol | $C_{11}H_9N_2ClO$ | 59.88 59.68 | 4.11 3.98 | 12.69 13.18 |
| 8[++] | 2-ethoxycar-bonyl-1-oxo-cyclopentane | 2-amino-3-hydroxy-pyridine | 2,3-trimethylene-9-hydroxy-4-oxo-4H-pyrido(1,2-a)-pyrimidine | 69 | 159 | 70% by weight ethanol | $C_{11}H_{10}N_2O_2$ | 65.33 65.22 | 4.98 5.12 | 13.86 13.74 |
| 9 | 2-ethoxycar-bonyl-1-oxo-cyclopentane | 2-amino-5-nitro-pyridine | 2,3-trimethylene-7-nitro-4-oxo-4H-pyrido(1,2-a)-pyrimidine | 45 | 168–169 | ethanol | $C_{11}H_9N_3O_3$ | 57.14 56.84 | 3.92 4.13 | 18.18 17.70 |
| 10 | 2-ethoxycar-bonyl-1-oxo-5-methyl-cyclopentane | 2-amino-6-methyl-pyridine | 2,3-(1-methyl-trimethylene)-6-methyl-4-oxo-4H-pyrido(1,2-a)-pyrimidine | 76 | 86–87 | ether | $C_{13}H_{14}N_2O$ | 72.86 72.74 | 6.59 6.71 | 13.08 13.12 |
| 11 | 2-ethoxycar-bonyl-1-oxo-4-tertiary-butyl-cyclo-pentane | 2-amino-6-methyl-pyridine | 2,3-(2-tertiary-butyl-trimethylene)-6-methyl-4-oxo-4H-pyrido(1,2-a)-pyrimidine | 57 | 147 | ether | $C_{16}H_{20}N_2O$ | 74.96 74.87 | 7.86 7.92 | 10.93 11.12 |
| 12[+++] | 2-ethoxycar-bonyl-1-oxo-cyclohexane | 2-amino-pyridine | 2,3-tetramethylene-4-oxo-4H-pyrido-(1,2-a)pyrimidine | 86 | 103–104 | diisopropyl ether | $Ch_{11}H_{10}N_2O$ | 71.98 71.87 | 6.04 6.09 | 13.99 14.02 |
| 13 | 2-ethoxycar-bonyl-1-oxo-cyclohexane | 2-amino-6-methyl-pyridine | 2,3-tetramethylene-6-methyl-4-oxo-4H pyrido(1,2-a)-pyrimidine | 67 | 122–123 | ethanol | $C_{13}H_{14}N_2O$ | 72.86 72.60 | 6.59 6.87 | 13.08 14.02 |
| 14 | 2-ethoxycar-bonyl-1-oxo-cyclohexane | 2-amino-3-hydroxy-pyridine | 2,3-tetramethylene-9-hydroxy-4-oxo-4H-pyrido(1,2-a)-pyrimidine | 71 | 129 | 70% by weight alcohol | $C_{12}H_{12}N_2O_2$ | 66.65 66.72 | 5.59 5.64 | 12.96 13.00 |
| 15 | 2-ethoxycar-bonyl-1-oxo-cycloheptane | 2-amino-pyridine | 2,3-pentamethylene-4-oxo-4H-pyrido-(1,2-a)pyrimidine | 84 | 136 | ethyl-acetate | $C_{13}H_{14}N_2O$ | 72.86 72.63 | 6.59 6.98 | 13.08 12.95 |
| 16 | 2-ethoxycar-bonyl-1-oxo-cycloheptane | 2-amino-6-methyl-pyridine | 2,3-pentamethylene-6-methyl-4-oxo-4H-pyrido(1,2-a)-pyrimidine | 61 | 97–98 | diisopropyl-ether | $C_{14}H_{16}N_2O$ | 73.65 73.50 | 7.06 7.20 | 12.27 12.66 |
| 17 | 2-ethoxycar-bonyl-1-oxo-cycloheptane | 2-amino-3-hydroxy-pyridine | 2,3-pentamethylene-9-hydroxy-4-oxo-4H-pyrido(1,2-a)-pyrimidine | 64 | 137–138 | 70% by weight ethanol | $C_{13}H_{14}N_2O_2$ | 68.00 67.92 | 5.84 6.04 | 11.70 12.31 |
| 18 | 2-ethoxycar-bonyl-1-oxo-cyclooctane | 2-amino-pyridine | 2,3-hexamethylene-4-oxo-4H-pyrido-(1,2-a)pyrimidine | 66 | 114–115 | diisopropyl-ether | $C_{14}H_{16}N_2O$ | 73.65 73.65 | 7.06 6.94 | 12.27 12.44 |
| 19 | 2-ethoxycar-bonyl-l-oxo-cyclooctane | 2-amino-bonyl-l-oxo-pyridine | 2,3-hexamethylene-6-methyl-4-oxo-4H-pyrido(1,2-a)-pyrimidine | 75 | 102 | ethanol | $C_{15}H_{18}N_2O$ | 74.35 74.20 | 7.49 7.32 | 11.56 11.39 |
| 20 | 2-ethoxycar-bonyl-1-oxo- | 2-amino-3-hydroxy- | 2,3-hexamethylene-9-hydroxy-4-oxo-pyrimidine | 62 | 156–158 | 70% by weight | $C_{14}H_{16}N_2O$ | 68.83 68.42 | 6.60 6.54 | 11.47 11.23 |

[x]The product is recovered by extraction with chloroform
[+] USP No. 3 965 100; Yield 60%; melting point 100°–102° C.
[++] USP No. 3 965 100; Yield 55%; melting point 136°–142° C.
[+++] J. Chem. Soc. C.: 1971, 2153; Yield 50%; melting point 101.5°–103° C.
[+++] J. Chem. Soc. C. 1970, 881; Yield 60%; melting point 99°–102° C.

EXAMPLES 21 to 35

0.1 mole of 2-ethoxycarbonyl-1-oxo-cycloalkane according to Table 3 and 0.1 mole of 2-amino-pyridine are stirred in a mixture of 28 ml. of phosphorus trichloride oxide and 7.0 g. of polyphosphoric acid for 3 hours at 100° C. The reaction mixture is decomposed at 70° to 80° C. with 100 ml. of ethanol. The mixture is cooled and the precipitated hydrochloride salt is filtered off and washed with ethanol, dried and crystallized from the given solvent. The prepared compounds and constants thereof are summarized in Table 3.

Table 3

| Example | Starting material 2-ethoxycarbonyl-1-oxo-cycloalkane | 2-amino-pyridine | Product | Yield % | Mp. °C. | Recrystallization solvent | Empirical formula | Analysis Calculated Found C % | H % | N % |
|---|---|---|---|---|---|---|---|---|---|---|
| 21 | 2-ethoxycarbonyl-1-oxo-cyclopentane | 2-amino-pyridine | 2,3-trimethylene-4-oxo-4H-pyrido-(1,2-a)pyrimidine-hydrochloride | 64 | 166–167 | ethanol-ether | $C_{11}H_{11}N_2ClO$ | 59.33 / 59.00 | 4.98 / 5.15 | 15.92 / 16.01 |
| 22 | 2-ethoxycarbonyl-1-oxo-cyclopentane | 2-amino-6-methyl-pyridine | 2,3-trimethylene-6-methyl-4-oxo-4H-pyrido(1,2-a)pyrimidine-hydrochloride | 67 | 221–224 | ethanol-ether | $C_{12}H_{13}N_2ClO$ | 60.89 / 60.45 | 5.54 / 5.49 | 14.98 / 14.51 |
| 23 | 2-ethoxycarbonyl-1-oxo-cyclopentane | 2-amino-5-methyl-pyridine | 2,3-trimethylene-7-methyl-4-oxo-4H-pyrido(1,2-a)pyrimidine-hydrochloride | 86 | 206–215 | ethanol | $C_{12}H_{13}N_2ClO$ | 60.89 / 60.74 | 5.54 / 5.21 | 14.98 / 14.64 |
| 24 | 2-ethoxycarbonyl-1-oxo-cyclopentane | 2-amino-4-methyl-pyridine | 2,3-trimethylene-8-methyl-4-oxo-4H-pyrido(1,2-a)-pyrimidine-hydrochloride | 80 | 202–210 | ethanol-ether | $C_{12}H_{13}N_2ClO$ | 60.89 / 60.37 | 5.54 / 6.11 | 14.98 / 14.94 |
| 25 | 2-ethoxycarbonyl-1-oxo-cyclopentane | 2-amino-3-methyl-pyridine | 2,3-trimethylene-9-methyl-4-oxo-4H pyrido(1,2-a)-pyrimidine-hydrochloride | 77 | 170–180 | ethanol-ether | $C_{12}H_{13}N_2ClO$ | 60.89 / 60.87 | 5.54 / 5.84 | 14.98 / 14.32 |
| 26 | 2-ethoxycarbonyl-1-oxo-cyclopentane | 2-amino-4,6-dimethyl-pyridine | 2,3-trimethylene-6,8-dimethyl-4-oxo-4H-pyrido(1,2-a)-pyrimidine-hydrochloride | 72 | 190–203 | ethanol-ether | $C_{13}H_{15}N_2ClO$ | 62.27 / 62.42 | 6.03 / 6.14 | 14.14 / 13.92 |
| 27 | 2-ethoxycarbonyl-1-oxo-cyclopentane | 2-amino-5-chloro-pyridine | 2,3-trimethylene-7-chloro-4-oxo-4H-pyrido(1,2-a)-pyrimidine-hydrochloride | 76 | 203–206 | ethanol | $C_{11}H_{10}N_2Cl_2O$ | 51.39 / 51.39 | 3.92 / 4.00 | 13.79 / 13.51 |
| 28 | 2-ethoxycarbonyl-1-oxo-5-methyl-cyclopentane | 2-amino-6-methyl-pyridine | 2,3-(1-methyl-trimethylene)-6-methyl-4-oxo-4H-pyrido(1,2-a)-pyrimidine-hydrochloride | 68 | 178–188 | ethanol-ether | $C_{13}H_{15}N_2ClO$ | 62.27 / 61.97 | 6.03 / 6.04 | 14.14 / 13.61 |
| 29 | 2-ethoxycarbonyl-1-oxo-4-tertiary-butyl-cyclopentane | 2-amino-6-methyl-pyridine | 2,3-(2-tertiary-butyl-trimethylene)-6-methyl-4-oxo-4H-pyrido(1,2-a)-pyrimidine-hydrochloride | 45 | 195–200 | ethanol-ether | $C_{16}H_{21}N_2ClO$ | 65.63 / 65.88 | 7.23 / 7.09 | 12.11 / 12.65 |
| 30 | 2-ethoxycarbonyl-1-oxo-cyclohexane | 2-amino-pyridine | 2,3-tetramethylene-4-oxo-4H-pyrido-(1,2-a)pyrimidine-hydrochloride | | | ethanol-ether | $C_{12}H_{13}N_2ClO$ | 60.89 / 60.56 | 5.54 / 5.56 | 14.98 / 14.91 |
| 31 | 2-ethoxycarbonyl-1-oxo-cyclohexane | 2-amino-6-methyl-pyridine | 2,3-tetramethylene-6-methyl-4-oxo-4H-pyrido(1,2-a)-pyrimidine-hydrochloride | 62 | 211–218 | ethanol-ether | $C_{13}H_{15}N_2ClO$ | 62.27 / 61.82 | 6.03 / 6.05 | 14.14 / 14.09 |
| 32 | 2-ethoxycarbonyl-1-oxo-cyclohexane | 2-amino-pyridine | 2,3-pentamethylene-4-oxo-4H-pyrido-(1,2-a)pyrimidine-hydrochloride | 81 | 175–181 | ethanol-ether | $C_{13}H_{15}N_2ClO$ | 62.27 / 62.20 | 6.04 / 5.77 | 14.14 / 14.08 |
| 33 | 2-ethoxycarbonyl-1-oxo-cycloheptane | 2-amino-6-methyl-pyridine | 2,3-pentamethylene-6-methyl-4-oxo-4H-pyrido(1,2-a)-pyrimidine-hydrochloride | 58 | 222–227 | ethanol-ether | $C_{14}H_{17}N_2ClO$ | 63.51 / 64.10 | 6.47 / 7.00 | 13.39 / 13.36 |
| 34 | 2-ethoxycarbonyl-1-oxo-cyclooctane | 2-amino-pyridine | 2,3-hexamethylene-4-oxo-4H-pyrido-(1,2-a)pyrimidine-hydrochloride | 62 | 192–203 | ethanol ether | $C_{14}H_{17}N_2ClO$ | 63.51 / 63.20 | 6.47 / 6.03 | 13.39 / 13.18 |
| 35 | 2-ethoxycarbonyl-1-oxo | 2-amino-6-methyl- | 2,3-hexamethylene-6-methyl-4-oxo-4H- | | | ethanol | | 64.62 | 6.87 | 12.72 |

Table 3-continued

| Example | Starting material 2-ethoxycar- bonyl-1-oxo- cycloalkane | 2-amino- pyridine | Product | Yield % | Mp. °C. | Recrystalli- zation solvent | Empirical formula | Analysis Calculated Found | | |
|---|---|---|---|---|---|---|---|---|---|---|
| | | | | | | | | C % | H % | N % |
| | cyclooctane | pyridine | pyrido(1,2-a)- pyrimidine-hydro- chloride | 68 | 200–206 | ether | $C_{15}H_{19}N_2ClO$ | 63.95 | 6.99 | 12.64 |

EXAMPLE 36

15.6 g. of 2-ethoxycarbonyl-1-oxo-cyclopentane and 10.8 g. of 2-amino-6-methyl-pyridine are stirred in a water-bath in the mixture of 28 ml. of phosphorus trichlorideoxide and 7.0 g. of polyphosphoric acid for 3 hours. The reaction mixture is cooled and decomposed cautiously with 50 ml. of water under external cooling with ice and neutralized with 10% by W/V sodium hydroxide solution. The precipitated oil is crystallized on triturating. The obtained crystals are filtered, washed with water, dried and crystallized from ethanol. 17 g. (85%) of 2,3-trimethylene-6-methyl-4-oxo-4H-pyrido(1,2-a) pyrimidine are obtained which product melts at 160° to 161° C. and by admixing it with the product of Example 2, the melting point is not depressed.

EXAMPLE 37

0.02 moles of 2-amino-pyridine-hydrochloride is boiled under reflux for 16 hours with 0.03 moles of 2-ethoxycarbonyl-1-oxo-cyclopentane in 50 ml. of pyridine. The solvent and the unreacted 2-ethoxycarbonyl-1-oxo-cyclopentane are distilled at reduced pressure and the residue is crystallized from a mixture of ethanol and ether. 2.15 g. (48%) of 2,3-trimethylene-4-oxo-4H-pyrido(1,2-a)pyrimidine hydrochloride are obtained, melting point: 222°–224° C. and admixed with the product according to Example 22. The melting point is not depressed.

EXAMPLE 38

The process is carried out as in Example 37 but as starting material 2-amino-pyridine-hydrobromide is used instead of 2-amino-pyridine hydrochloride and after a reaction lasting 8 hours 3.3 g. (62%) of 2,3-trimethylene-4-oxo-4H-pyrido(1,2-a) pyrimidine hydrobromide are obtained, melting point 275°–277° C. (recrystallized from ethanol).

Analysis for the formula $C_{11}H_{11}N_2BrO$ Calculated: C, 49.46%; H, 4.15%; N, 10.49%; Br, 29.91%; Found: C, 49.80%; H, 4.37%; N, 10.62%; Br, 29.85%.

The base is set free from the hydrobromide salt by the usual methods and it is recrystallized from ethanol. 2,3-trimethylene-4-oxo-4H-pyrido(1,2-z)pyrimidine is obtained which when admixed with the product according to Example 1 does not given any melting point depression.

EXAMPLE 39

The reaction is carried out according to Example 37, but 2-amino-pyridine hydroiodide is used instead of 2-amino-pyridine-hydrochloride; the reaction lasts 6 hours and 4.74 g. (76%) of 2,3-trimethylene-4-oxo-4H-pyrido(1,2-a)pyrimidine-hydroiodide are obtained, the product is recrystallized from ethanol and it melts at 212° to 214° C.

Analysis for the formula $C_{11}H_{11}N_2IO$: Calculated: C, 42.06%; H, 3.53%; N, 8.92%; I, 40.40%; Found: C, 41.85%, H, 3.60%; N, 9.09%; I, 40.21%.

EXAMPLE 40

2.31 g. of 2,3-trimethylene-7-nitro-4-oxo-4H-pyrido(1,2-a)pyrimidine and 3.9 g. of powdered iron are suspended in 20 ml of water. The reaction mixture is stirred for 3 hours on a water bath, while 3 to 4 ml. of hydrochloric acid are added dropwise. The mixture is filtered on a draped filter, the filtrate is neutralized with 10% by W/V sodium hydroxide solution and the precipitated fluffy substance is concentrated by heating. The obtained reaction mixture is shaken out three times with chloroform. The combined chloroform solution is dried over sodium sulphate, filtrated and evaporated. 0.72 g. (35%) of yellow 2,3-trimethylene-7-amino-4-oxo-4H-pyrido(1,2-a)pyrimidine is obtained and recrystallized from ethanol, melting point: 260°–264° C.

Analysis for the formula $C_{11}H_{11}N_3O$: Calculated: C, 65.67%; H, 5.51%; N, 20.88%; Found: C, 65.33%; H, 5.40%, N, 20.86%.

EXAMPLE 41

2.0 g. of 2,3-trimethylene-6-methyl-4-oxo-4H-pyrido(1,2-a)pyrimidine are dissolved in 25 ml. of acetone and the solution together with 7.1 g. of methyl iodide is filled to a bomb tube. The sealed bomb tube is maintained at 100° C. for 10 hours. The reaction mixture is cooled and the bomb tube is opened followed by evaporation to a volume of 15 ml. The reaction mixture is allowed to stand overnight and the precipitated crystals are filtered off, and covered with a small amount of acetone, 2.15 g. (67%) of yellow 1,6-dimethyl-2,3-trimethylene-4-oxo-4H-pyrido(1,2-a)pyrimidinium iodide are obtained, the product is recrystallized from ethanol, m.p. 228°–230° C.

Analysis for the formula $C_{13}H_{15}N_2OI$: Calculated: C, 45.63%; H, 4.42%; Found: C, 45.62%; H, 4.43%.

EXAMPLE 42

4.0 g. of 2,3-trimethylene-6-methyl-4-oxo-4H-pyrido(1,2-a)pyrimidine are dissolved in 50 ml. of acetone and after adding 2.52 g. of dimethylsulfate the mixture is boiled for 16 hours. The reaction mixture is then evaporated to about half volume. The product precipitates on cooling in the form of crystals. The precipitated crystals are filtered and washed with acetone. 4.96 g. (76%) of 1,6-dimethyl-2,3-trimethylene-4-oxo-4H-pyrido(1,2-a)pyrimidinium methyl-sulphate are obtained and crystallized from a mixture of ethanol and ether. M.p.: 148°–150° C.

Analysis for the formula $C_{14}H_{18}N_2O_5S$: Calculated: C, 51.52%; H, 5.56%; N, 8.58%; Found: C, 51.98%; H, 5.58%; N, 8.53%.

EXAMPLES 43 TO 52

20 mmoles of 4-oxo-4H-pyrido(1,2-a)pyrimidine according to Table 4 are dissolved in 50 ml. of ethanol and the solution is hydrogenated for 3 to 6 hours in the presence of 5 g. of Raney nickel catalyst at atmospheric pressure. The theoretical amount of hydrogen is consumed whereafter the hydrogen takeup ceases. The catalyst is removed by filtration, the solution is evaporated and the residue is crystallized from the given solvent. The prepared compounds are enumerated in Table 4.

EXAMPLES 53 TO 61

20 mmoles of 4-oxo-4H-pyrido(1,2-a)pyrimidine according to Table 5 are dissolved in 50 ml. of ethanol and the solution is hydrogenated in the presence of 1 g. 10% by weight palladium on charcoal catalyst at atmospheric pressure. The calculated amount of hydrogen is consumed within 6 to 10 hours. The catalyst is filtered off and the reaction mixture is evaporated and crystalized from the given solvent. The prepared compounds are shown in Table 5.

Table 4

| Example | Starting material | Product | Catalyst | Yield % | Mp. °C. | Recrystallization solvent | Empirical formula | Analysis Calculated Found C % | H % | N % |
|---|---|---|---|---|---|---|---|---|---|---|
| 43 | 2,3-trimethylene-4-oxo-4H-pyrido(1,2-a)pyrimidine | 2,3-trimethylene-4-oxo-6,7,8,9-tetrahydroxo-4H-pyrido(1,2-a)-pyrimidine | Raney Ni | 96 | 96–97 | petrol-ether | $C_{11}H_{14}N_2O$ | 69.44<br>69.30 | 7.42<br>7.59 | 14.73<br>14.89 |
| 44+ | 2,3-tetramethylene-4-oxo-4H-pyrido-(1,2-a)pyrimidine | 2,3-tetramethylene-4-oxo-6,7,8,9-tetrahydro-4H-pyrido(1,2-a)-pyrimidine | Raney Ni | 98 | 172–173++ | n-hexane | $C_{12}H_{16}N_2O$ | 70.56<br>70.45 | 7.90<br>8.00 | 13.72<br>13.74 |
| 45 | 2,3-pentamethylene-4-oxo-4H-pyrido(1,2-a)-pyrimidine | 2,3-pentamethylene-4-oxo-6,7,8,9-tetrahydro-4H-pyrido(1,2-a)-pyrimidine | Raney Ni | 95 | 159 | n-hexane | $C_{13}H_{18}N_2O$ | 71.52<br>71.49 | 8.31<br>8.22 | 12.83<br>12.94 |
| 46 | 2,3-hexamethylene-4-oxo-4H-pyrido(1,2-a)-pyrimidine | 2,3-hexamethylene-4-oxo-6,7,8,9-tetrahydro-4H-pyrido(1,2-a)-pyrimidine | Raney Ni | 97 | 110 | n-hexane | $C_{14}H_{20}N_2O$ | 72.38<br>72.22 | 8.68<br>8.64 | 12.06<br>12.09 |
| 47 | 2,3-trimethylene-4-oxo-4H-pyrido(1,2-a)-pyrimidine | 2,3-trimethylene-6-methyl-4-oxo-6,7,8,9-tetrahydro-4H-pyrido(1,2-a)-pyrimidine | Raney Ni | 96 | 86–87 | petrol-ether | $C_{12}H_{16}N_2O$ | 70.56<br>70.44 | 7.90<br>7.85 | 13.72<br>13.80 |
| 48 | 2-tetramethylene-6-methyl-4-oxo-4H-pyrido-(1,2-a)pyrimidine | 2,3-tetramethylene-6-methyl-4-oxo-6,7,8,9-tetrahydro-4H-pyrido(1,2-a)-pyrimidine | Raney Ni | 97 | 128–130 | n-hexane | $C_{13}H_{18}N_2O$ | 71.52<br>71.49 | 8.31<br>8.22 | 12.83<br>12.94 |
| 49 | 2,3-pentamethylene-6-methyl-4-oxo-4H-pyrido-(1,2-a)-pyridomidine | 2,3-pentamethylene-6-methyl-4-oxo-6,7,8,9-tetrahydro-4H-pyrido(1,2-a)-pyrimidine | Raney Ni | 98.5 | 93–94 | petrol-ether | $C_{14}H_{20}N_2O$ | 72.38<br>72.44 | 8.68<br>8.81 | 12.06<br>12.04 |
| 50 | 2,3-hexamethylene-6-methyl-4-oxo-4H-pyrido-(1,2-a)pyrimidine | 2,3-hexamethylene-6-methyl-4-oxo-6,7,8,9-tetrahydro-4H-pyrido(1,2-a)-pyrimidine | Raney Ni | 94.5 | 70–71 | petrol-ether | $C_{15}H_{22}N_2O$ | 73.13<br>73.04 | 9.00<br>9.10 | 11.37<br>11.32 |
| 51 | 2,3-(1-methyl-trimethylene)-6-methyl-4-oxo-4H-pyrido(1,2-a)-pyrimidine | 2,3-(1-methyl-trimethylene)-6-methyl-4-oxo-6,7,8,9-tetrahydro-4H-pyrido-(1,2-a)pyrimidine | Raney Ni | 96 | 88–91 | n-hexane | $C_{13}H_{18}N_2O$ | 71.52<br>71.49 | 8.31<br>8.22 | 12.83<br>12.94 |
| 52 | 2,3-(2-tertiary-butyl-trimethylene)-6-methyl-4-oxo-4H-pyrido-(1,2-a)pyrimidine | 2,3-(2-tertiary-butyl-trimethylene)-6-methyl-4-oxo-6,7,8,9-tetrahydro-4H-pyrido(1,2-a)-pyrimidine | Raney Ni | 95.5 | 98–100 | ether | $C_{16}H_{24}N_2O$ | 73.80<br>73.76 | 9.29<br>9.34 | 10.76<br>10.76 |

+Melting point of hydrochloride salt 185°–195° C. (ethanol-ether)
++J. Org. Chem. 40, 2201, 1975; Yield 14%; melting point 168°–170° C.

Table 5

| Example | Starting material | Product | Catalyst | Yield % | Mp. °C. | Recrystallization solvent | Empirical formula | Analysis Calculated / Found | | |
|---|---|---|---|---|---|---|---|---|---|---|
| | | | | | | | | C % | H % | N % |
| 53 | 2,3-trimethylene-4-oxo-4H-pyrido(1,2-a)-pyrimidine | 2,3-trimethylene-4-oxo-6,7,8,9-tetrahydro-4H-pyrido-(1,2-a)pyrimidine | Pd/C | 97 | 97 | petrol-ether | $C_{11}H_{14}N_2O$ | 69.44 / 69.40 | 7.42 / 7.41 | 14.73 / 14.78 |
| 54 | 2,3-tetramethylene-4-oxo-4H-pyrido(1,2-a)-pyrimidine | 2,3-tetramethylene-4-oxo-6,7,8,9-tetrahydro-4H-pyrido(1,2-a)-pyrimidine | Pd/C | 98.5 | 172–173+ | n-hexane | $C_{12}H_{16}N_2O$ | 70.56 / 70.63 | 7.90 / 7.82 | 13.72 / 13.80 |
| 55 | 2,3-pentamethylene-4-oxo-4H-pyrido(1,2-a)-pyrimidine | 2,3-pentamethylene-4-oxo-6,7,8,9-tetrahydro-4H-pyrido(1,2-a)-pyrimidine | Pd/C | 94.5 | 158–159 | n-hexane | $C_{13}H_{18}N_2O$ | 71.52 / 71.42 | 8.31 / 8.25 | 12.83 / 13.01 |
| 56 | 2,3-hexamethylene-4-oxo-4H-pyrido(1,2-a)-pyrimidine | 2,3-hexamethylene-4-oxo-6,7,8,9-tetrahydro-4H-pyrido(1,2-a)-pyrimidine | Pd/C | 96 | 110 | n-hexane | $C_{14}H_{20}N_2O$ | 72.38 / 72.31 | 8.68 / 8.72 | 12.06 / 12.10 |
| 57 | 2,3-trimethylene-6-methyl-4-oxo-4H-pyrido-(1,2-a)pyrimidine | 2,3-trimethylene-6-methyl-4-oxo-6,7,8,9-tetrahydro-4H-pyrido(1,2-a)-pyrimidine | Pd/C | 94 | 86–87 | petrol-ether | $C_{12}H_{16}N_2O$ | 70.56 / 70.51 | 7.90 / 7.98 | 13.72 / 13.69 |
| 58 | 2,3-tetramethylene-6-methyl-4-oxo-4H-pyrido-(1,2-a)-pyrimidine | 2,3-tetramethylene-6-methyl-4-oxo-6,7,8,9-tetrahydro-4H-pyrido-(1,2-a)-pyrimidine | Pd/C | 98 | 129–130 | n-hexane | $C_{13}H_{18}N_2O$ | 71.52 / 71.60 | 8.31 / 8.28 | 12.83 / 12.85 |
| 59 | 2,3-pentamethylene-6-methyl-4-oxo-4H-pyrido-(1,2-a)-pyrimidine | 2,3-pentamethylene-6-methyl-4-oxo-6,7,8,9-tetrahydro-4H-pyrido-(1,2-a)-pyrimidine | Pd/C | 96 | 94 | petrol-ether | $C_{14}H_{20}N_2O$ | 72.38 / 72.25 | 8.68 / 8.72 | 12.06 / 12.10 |
| 60 | 2,3-hexamethylene-6-methyl-4-oxo-4H-pyrido-(1,2-a)-pyrimidine | 2,3-hexamethylene-6-methyl-4-oxo-6,7,8,9-tetrahydro-4H-pyrido-(1,2-a)-pyrimidine | Pd/C | 97.5 | 70–71 | petrol-ether | $C_{15}H_{22}N_2O$ | 73.13 / 73.21 | 9.00 / 8.95 | 11.37 / 11.44 |
| 61 | 2,3-(1-methyl-trimethylene)-6-methyl-4-oxo-4H-pyrido(1,2-a)-pyrimidine | 2,3-(1-methyl-trimethylene)-6-methyl-4-oxo-6,7,8,9-tetrahydro-4H-pyrido-(1,2-a)-pyrimidine | Pd/C | 96.5 | 89–91 | n-hexane | $C_{13}H_{18}N_2O$ | 71.52 / 71.48 | 8.31 / 8.42 | 12.83 / 12.75 |
| 62 | 2,3-(2-tertiary-butyl-trimethylene)-6-methyl-4-oxo-4H-pyrido-(1,2-a)-pyrimidine | 2,3-(2-tertiary-butyl-trimethylene)-6-methyl-4-oxo-6,7,8,9-tetrahydro-4H-pyrido-(1,2-a)-pyrimidine | Pd/C | 98 | 99–100 | ether | $C_{16}H_{24}N_2O$ | 73.80 / 73.84 | 9.29 / 9.30 | 10.76 / 10.87 |

+J. Org. Chem. 40, 2201, 1975; yield 14%; melting point 168° to 170° C.

EXAMPLE 63

2.7 g. of 2-amino-3,4,5,6-tetrahydro-pyridine hydrochloride are treated in 20 ml. of ethanol with an equivalent amount of sodium ethylate. The precipitated sodium chloride is removed by filtration and 3.4 g. of 2-ethoxycarbonyl-1-oxo-cyclohexane are added to the obtained solution, followed by the boiling of the reaction mixture for 1 hour. The reaction mixture is evaporated. The residue is crystallized from a mixture of acetone and hexane. 3.02 g. (74%) of 2,3-tetramethylene-4-oxo-6,7,8,9-tetrahydro-4H-pyrido(1,2-a)pyrimidine are obtained, melting point: 171°–172° C. and no melting point depression is shown by admixing the product with the product of Example 44 or 54.

EXAMPLE 64 to 67

55 mmoles of 2-amino-1-cyclohexane-carboxylic acid according to Table 6 and 5 mmoles of lactimether are boiled for 5 hours in 20 ml. of chlorobenzene and the reaction mixture is evaporated to dryness and the residue is dissolved with 4×25 ml. of ether. The ether solution is evaporated. The obtained product is recrystallized from the given solvent according to Table 6. The prepared products and data thereof are shown in Table 6.

Table 6

| Example | Starting material 2-amino-1-cyclohexane-carboxylic acid | lacti-mether | Product | Yield % | Mp. °C. | Recrystallization solvent | Empirical formula | Analysis Calculated Found | | |
|---|---|---|---|---|---|---|---|---|---|---|
| | | | | | | | | C % | H % | N % |
| 64 | cis-2-amino-1-cyclohexane-carboxylic acid | 2-ethoxy-3,4,5,6-tetrahydro-pyridine | 2,3-cis-2,3-(tetramethylene)-4-oxo-6,7,2,3,8,9-hexahydro-4H-pyrido-(1,2-a)pyrimidine | 88 | 68–71 | ether | $C_{12}H_{18}N_2O$ | 69.87 69.44 | 8.80 8.66 | 13.58 13.46 |
| 65 | trans-2-amino-1-cyclohexane-carboxylic acid | 2-ethoxy-3,4,5,6-tetrahydro-pyridine | 2,3-trans-(tetramethylene)-4-oxo-2,3,6,7,8,9-hexahydro-4H-pyrido-(1,2-a)pyrimidine | 79 | 129–130 | petrol-ether | $C_{12}H_{18}N_2O$ | 69.87 69.71 | 8.80 8.81 | 13.58 13.62 |
| 66 | cis-2-amino-1-cyclohexane-carboxylic acid | 2-ethoxy-4,5,6,7-tetrahydro-3H-azepine | 2,3-cis-(tetramethylene)-4-oxo-2,3,4,6,7,8,9,10-octahydro-azepino-(1,2-a)pyrimidine | 55 | 81–82+ | ether | $C_{13}H_{20}N_2O$ | 70.87 71.36 | 9.15 8.92 | 12.72 12.61 |
| 67 | cis-2-amino-1-cyclohexane carboxylic acid | 2-ethoxy 5-tertiary-butyl-4,5,-6,7-tetrahydro-3H-azepine | 2,3-cis-(tetramethylene)-8-tertiary butyl-4-oxo-2,3,4,6,-7,8,9,10-octahydro-azepino-(1,2-a)-pyrimidine | 74 | 96–100 | n-hexane | $C_{17}H_{28}N_2O$ | 73.86 73.57 | 10.21 10.17 | 10.13 10.25 |

+GFR Pat. No. 1 088 968. Melting point 100° C.

EXAMPLES 68 to 71

5 mmoles of tricyclic nitrogen bridge-head compounds are dissolved in 5 ml. of methanol and 10 mmoles of sodiumborohydride dissolved in 10 ml. of water are added dropwise to the methanolic solution under shaking. After 2 hours reaction time the excess of the reducing agent is decomposed with a few drops of acetic acid and the excess of acetic acid is neutralized with sodiumbicarbonate solution. The methanol is distilled off and the aqueous part is extracted with 3×20 ml. of ether and evaporated after drying. The white crystalline residue is crystallized from ether. The prepared products and data thereof are shown in Table 7.

solved in 50 ml. of acetone and 20 mmoles of dimethyl-sulphate are added to the reaction mixture which is boiled for 8 hours. The acetone is evaporated to half volume and after cooling the precipitated crystals are filtered and covered with a small amount of acetone. 73.5% of white 1,6-dimethyl-2,3-trimethylene-4-oxo-6,7,8,9-tetrahydro-4H-pyrido(1,2-a)pyrimidinium methylsulphate is obtained, which after recrystallization from a mixture of acetone and ether melts at 129° to 132° C.

Analysis for the formula $C_{14}H_{22}N_2O_5S$: Calculated: C, 50.90%; H, 6.71%; N, 8.47%; Found: C, 50.52%; H, 6.77%; N, 8.32%.

Table 7

| Example | Starting material tricyclic compound having nitrogen bridge-head | Product | Yield % | Mp. °C. | Recrystallization solvents | Empirical formula | Analysis Calculated Found | | |
|---|---|---|---|---|---|---|---|---|---|
| | | | | | | | C % | H % | N % |
| 68 | 2,3-cis-(tetramethylene)-4-oxo-2,3,6,7,8,9-hexahydro-4H-pyrido-(1,2-a)pyrimidine | 2,3-cis-(tetramethylene)-4-oxo-1,2,3,6,7,8,9,9a-octahydro-4H-pyrido(1,2-a)pyrimidine | 76 | 111–113 | ether | $C_{12}H_{20}N_2O$ | 69.19 69.22 | 9.68 9.74 | 13.45 14.51 |
| 69 | 2,3-trans-(tetramethylene)-4-oxo-2,3,6,-7,8,9-hexahydro-4H-pyrido(1,2-a)pyrimidine | 2,3-trans-(tetramethylene)-4-oxo-1,2,3,6,7,8,9,9a-octahydro-4H-pyrido-(1,2-a)pyrimidine | 77 | 175–176 | ether | $C_{12}H_{20}N_2O$ | 69.19 69.07 | 9.68 9.46 | 13.45 13.39 |
| 70 | 2,3-cis-(tetramethylene-4-oxo-2,3,4,6,7,8,9,10-octahydro-azepino (1,2-a) pyrimidine | 2,3-cis-(tetramethylene)-4-oxo-1,2,3,4,6,7,8,9,10,10a-decahydro-azepino-(1,2-a) pyrimidine | 72 | 126–128 | ether | $C_{13}H_{22}N_2O$ | 70.23 70.16 | 9.97 9.89 | 12.60 12.62 |
| 71+ | 2,3-cis-(tetramethylene)-8-tertiary-butyl-4-oxo-2,3,4,6,7,8,9,10-octahydro-azepino (1,2-a) pyrimidine | 2,3-cis-(tetramethylene)-8-tertiary-butyl-4-oxo-1,2,3,4,6,7,8,9,10,10a-decahydro-azepino-(1,2-a)pyrimidine | 70 | 154–156 | ether | $C_{17}H_{30}N_2O$ | 73.33 73.20 | 10.86 10.72 | 10.06 9.98 |

+Hydrochloride salt melts at 258°–261° C. (ethanol-ether)

EXAMPLE 72

20 mmoles of 2,3-trimethylene-6-methyl-4-oxo-6,7,8,9-tetrahydro-4H-pyrido(1,2-a)pyrimidine are dis-

EXAMPLE 73

The reaction is set forth as in Example 72 but 2,3-tetramethylene-6-methyl-4-oxo-6,7,8,9-tetrahydro-4H- pyrido(1,2-a)pyrimidine is substituted for 2,3-trimethylene-6-methyl-4-oxo-6,7,8,9-tetrahydro-4H-pyrido(1,2-a)pyrimidine and thus snowwhite 1,6-dimethyl-2,3-tetramethylene-4-oxo-6,7,8,9-tetrahydro-4H-pyrido(1,2-a)pyrimidinium methyl sulphate is obtained with a yield of 71%, which is crystallized from acetone and melts at 155°–157° C.

Analysis for $C_{15}H_{24}N_2O_5S$: Calculated: C, 52.31%; H, 7.02%; N, 8.12%; Found: C, 52.53%; H, 7.08%; N, 8.06%.

EXAMPLE 74

3.3 g. of 1,6-dimethyl-2,3-trimethylene-6,7,8,9-tetrahydro-4H-pyrido(1,2-a)pyrimidinium methyl sulphate are dissolved in 15 ml. of water and a solution of 10 mmoles of sodiumborohydride in 10 ml. of water is added under shaking. The reaction mixture is heated to 34° to 45° C. After 2 hours' reaction time the excess of the reducing agent is decomposed with acetic acid and the excess of the acid is neutralized with sodium bicarbonate. The reaction mixture is shaken out with 3×25 ml. of chloroform. The chloroform solution is evaporated after drying. The residue is distilled in vacuo from a Hickmann flask. The main cut is distilled at 128°–129° C. at 4 Hg mm. 1.8 g. (81%) of 1,6-dimethyl-2,3-trimethylene-4-oxo-1,2,3,6,7,8,9,9a-octahydro-4H-pyrido(1,2-a)pyrimidine is obtained in the form of a non-crystallizable oil. The hydrochloride salt obtained from the product melts at 223°–227° C. after recrystallization from ethanol-ether mixture.

Analysis for the formula $C_{13}H_{22}N_2O\cdot HCl$: Calculated: C, 60.34%; H, 8.96%; $Cl_{ionic}$, 13.70%; Found: C, 60.41%; H, 9.12%; $Cl_{ionic}$, 13.28%.

EXAMPLE 75

15.6 g. of 2-ethoxycarbonyl-1-oxo-cyclopentane and 11.1 g. of 2-amino-3-hydroxy-pyridine are reacted according to Example 36 and thus 10.2 g. of crystalline 2.3-trimethylene-9-hydroxy-4-oxo-4H-pyrido(1,2-a)pyrimidine are obtained, m.p. 152°–156° C. and after recrystallization from 70% ethanol the product did not show any melting point depression with the compound prepared according to Example 8.

EXAMPLE 76

2-Amino-4-methyl-pyridine-hydrochloride was reacted with 2-ethoxy-carbonyl-1-oxo-cyclopentane according to Example 37 and thus 2.08 g. (44%) of 2,3-trimethylene-8-methyl-4-oxo-4H-pyrido(1,2-a)pyrimidine-hydrochloride was obtained, melting point: 200°–205° C. and thus no melting point depression is given with a compound obtained according to Example 24.

EXAMPLE 77

0.02 moles of 2-ethoxycarbonyl-1-imino-cyclopentane and 0.02 moles of 2-methoxy-3,4,5,6-tetrahydropyridine are stirred in 20 g. of polyphosphoric acid for 30 minutes at 70° C. and for 30 minutes at 120° C. The reaction mixture is diluted with 20 ml. of water and the pH-value of the solution is adjusted with 10% by W/V sodium hydroxide solution to neutral. The solution is extracted with 3×25 ml. of chloroform and the combined extract is evaporated after drying. The yellow residue is chromatographed with 30 g. of alumina of activity II (solvent: petrolether) and the obtained fractions are analyzed by thin layer chromatography, (silicagel plate, benzene:ethanol:4:1) and the corresponding fractions are evaporated and thus 0.38 g. (10%) of 2,3-trimethylene-4-oxo-6,7,8,9-tetrahydro-4H-pyrido(1,2-a)pyrimidine are obtained, melting point: 95°–96° C., and the product does not give any melting point depression with the product of the Example 43 or 53.

EXAMPLE 78

0.02 moles of 2-iminopyrrolidine-hydrochloride is reacted with an equivalent amount of sodium ethylate and 2-ethoxycarbonyl-1-oxo-cyclohexane according to Example 63. 2,3-trimethylene-6,7,8,9-tetrahydro-4-oxoquinazoline is obtained. Yield: 63%. The mixture is crystallized from a mixture of acetone and hexane. Melting point: 120°–121° C.

Analysis for the formula $C_{11}H_{14}N_2O$: Calculated: C, 69.44%; H, 7.42%; N, 14.73%; Found: C, 69.23%; H, 7.40%; N, 14.91%.

EXAMPLE 79

0.02 moles of 2-ethoxycarbonyl-1-oxo-cyclohexane is reacted with 0.02 moles of 2-amino-nicotinic acid according to Examples 1 to 20. 2,3-tetramethylene-9-carboxy-4-oxo-4H-pyrido(1,2-a)pyrimidine is formed. Yield: 46%. The product is recrystallized from ethanol, melting point: 202°–204° C.

Analysis for the formula $C_{13}H_{12}N_2O_3$: Calculated: C, 63.92%; H, 4.95%; Found: C, 63.96%; H, 4.95%.

EXAMPLE 80

0.02 moles of 2-ethoxycarbonyl-1-oxo-cyclohexane is reacted with 0.02 moles of 2-amino-3-ethoxycarbonyl-pyridine according to Example 1 to 20. 2,3-tetramethylene-9-ethoxycarbonyl-4-oxo-4H-pyrido(1,2-a)pyrimidine is obtained. Yield: 63%. After recrystallization from ethanol the product melts at 143°–144° C.

Analysis for the formula $C_{15}H_{16}N_2O_3$: Calculated: C, 66.16%; H, 5.92%; Found: C, 66.20%; H, 5.87%.

EXAMPLE 81

1 g. of 2,3-tetramethylene-9-carboxy-4-oxo-4H-pyrido(1,2-a)pyrimidine (of Example 79) is refluxed for 3 hours in 20 ml. of 20% W/V by of ethanol containing hydrochloric acid. The solution is evaporated to dryness and thus yellow crystals are obtained, which are dissolved in 25 ml. of water and neutralized with saturated sodiumbicarbonate solution. The precipitated 0.92 g. of (82%) of 2,3-tetramethylene-9-ethoxycarbonyl-4-oxo-4H-pyrido(1,2-a)pyrimidine is recrystallized from ethanol, melting point: 144°–145° C. The product does not give any melting point depression with the product of Example 80.

EXAMPLE 82

0.02 moles of 2-ethoxycarbonyl-1-oxo-cyclohexane is reacted with 0.02 moles of 6-aminonicotinic acid according to Example 1 to 20. 2,3-tetramethylene-7-carbamoyl-4-oxo-4H-pyrido(1,2-a)pyrimidine is obtained. Yield: 41%. Melting point after recrystallization 313°–315° C.

Analysis for the formula $C_{13}H_{13}N_3O_2$: Calculated: C, 64.18%; H, 5.39%; N, 17.28%; Found: C, 64.22%; H, 5.61%.

EXAMPLE 83

0.02 moles of 2-ethoxycarbonyl-1-oxo-cyclohexane is reacted with 0.02 moles of 2-amino-5-ethoxycarbonyl-pyridine according to Examples 1 to 20. 2,3-tetramethylene-7-ethoxycarbonyl-4-oxo-4H-pyrido(1,2-a)pyrimidine is obtained. Yield: 67%. Melting point after recrystallization from ether: 100°-102° C.

Analysis for the formula $C_{15}H_{16}N_2O_3$: Calculated: C, 66.16%; H, 5.92%; Found: C, 66.20%; H, 6.02%.

EXAMPLE 84

0.02 moles of 2-ethoxycarbonyl-1-oxo-cyclohexane is reacted with 0.02 moles of 6-amino-nicotinic acid according to Example 36. 2,3-tetramethylene-7-carboxy-4-oxo-4H-pyrido(1,2-a)pyrimidine is obtained. Yield: 44%. After recrystallization from ethanol the product melts at 256°-258° C.

Analysis for the formula $C_{13}H_{12}N_2O_3$: Calculated: C, 63.92%; H, 4.95%; Found: C, 63.84%; H, 5.00%.

EXAMPLE 85

0.02 moles of 2-ethoxycarbonyl-1-oxo-cyclohexane and 0.02 moles of 6-amino-nicotinic acid are stirred for 2 hours at 110° C. in the mixture of 10 ml. of phosphorus trichloride oxide and 2 g. of polyphosphoric acid. The reaction mixture is decomposed with 20 ml. of ethanol at 70° to 80° C. and the solution is neutralized under cooling with ice with a 10% by W/V solution hydroxide solution. The ethanol is evaporated and the residue is extracted with 4×25 ml. of chloroform. The combined extract is evaporated after drying and the residue is crystallized after trituration with ether. 2,3-tetramethylene-7-ethoxycarbonyl-4-oxo-4H-pyrido(1,2-a)pyrimidine is obtained, yield: 40%. The product is recrystallized from ether, melting point: 101°-102° C., the product does not give melting point depression with the product according to Example 83.

EXAMPLE 86

0.02 moles of 2-ethoxycarbonyl-1-oxo-cyclohexane is reacted with 0.02 moles of 2-amino-5-ethoxycarbonyl-pyridine according to Example 85. 2,3-Tetramethylene-7-ethoxycarbonyl-4-oxo-4H-pyrido(1,2-a)pyrimidine is obtained. Yield: 49%. The product is recrystallized from ether, melting point: 100°-102° C. The product does not give melting point depression with a product of Example 83 or 85.

EXAMPLE 87

2,3-tetramethylene-7-carboxy-4-oxo-4H-pyrido(1,2-a)pyrimidine prepared according to Example 84 is esterified with ethanol as in Example 81. 2,3-Tetramethylene-7-ethoxycarbonyl-4-oxo-4H-pyrido(1,2-a)pyrimidine is obtained. Yield: 91%. After recrystallization from ether the melting point is at 101°-102° C., no melting point depression is given when admixed with the products according to Examples 83, 85 and 86.

EXAMPLE 88

2.82 (0.02 moles) of 2-oxocyclohexane-1-carboxamide and 1.88 g. (0.02 moles) of 2-amino-pyridine are heated in 20 g. of polyphosphoric acid on waterbath under stirring for 1.5 hours. The reaction mixture is poured to 20 ml. of water and neutralized with 10% by W/V sodium hydroxide solution. The precipitated crystals are filtered and washed with water. 2.6 g. (46%) of 2,3-tetramethylene-4-oxo-4H-pyrido(1,2-a)pyrimidine are obtained. After recrystallization from diisopropylether the product melts at 103° C. and no melting point depression is given when admixed with the product prepared according to Example 12.

What we claim is:

1. A compound of the formula:

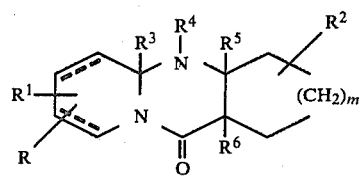

wherein

R is a 6- or a 7-position halogen, $C_1$ to $C_4$ alkyl, nitro, amino, carboxy, methoxycarbonyl, ethoxycarbonyl or carbamoyl;

$R^1$ is a 6- or a 7-position hydrogen or $C_1$ to $C_4$ alkyl or is 8-methyl;

$R^2$ is hydrogen or $C_1$ to $C_4$ alkyl;

$R^3$ is hydrogen;

$R^4$ is hydrogen or $C_1$ to $C_4$ alkyl or $R^3$ and $R^4$ form a chemical bond;

$R^5$ is hydrogen;

$R^6$ is hydrogen or $R^5$ and $R^6$ form a chemical bond; and m is 1 or 2;

or a pharmaceutically acceptable acid addition or quaternary salt thereof.

2. The compound defined in claim 1 selected from the group which consists of:

2,3-trimethylene-6-methyl-4-oxo-4H-pyrido(1,2-a)pyrimidine;

2,3-trimethylene-7-methyl-4-oxo-4H-pyrido(1,2-a)pyrimidine;

2,3-trimethylene-6,8-dimethyl-4-oxo-4H-pyrido(1,2-a)pyrimidine;

2,3-trimethylene-7-chloro-4-oxo-4H-pyrido(1,2-a)pyrimidine;

2,3-trimethylene-7-nitro-4-oxo-4H-pyrido(1,2-a)pyrimidine;

2,3-(1-methyl-trimethylene)-6-methyl-4-oxo-4H-pyrido(1,2-a)pyrimidine:

2,3-(2-t-butyl-trimethylene)-6-methyl-4-oxo-4H-pyrido(1,2-a)pyrimidine;

2,3-tetramethylene-6-methyl-4-oxo-4H-pyrido(1,2-a)pyrimidine;

2,3-trimethylene-7-amino-4-oxo-4H-pyrido(1,2-a)pyrimidine;

2,3-trimethylene-6-methyl-4-oxo-6,7,8,9-tetrahydro-4H-pyrido(1,2-a)-pyrimidine;

2,3-tetramethylene-6-methyl-4-oxo-6,7,8,9-tetrahydro-4H-pyrido(1,2-a)-pyrimidine;

2,3-(1-methyl-trimethylene)-6-methyl-4-oxo-6,7,8,9-tetrahydro-4H-pyrido(1,2-a)pyrimidine;

2,3(2-t-butyl-trimethylene)-6-methyl-4-oxo-6,7,8,9-tetrahydro-4H-pyrido(1,2-a)pyrimidine;

2,3-tetramethylene-7-ethoxycarbonyl-4-oxo-4H-pyrido(1,2-a)pyrimidine; and 2,3-tetramethylene-7-carboxy-4-oxo-4H-pyrido(1,2-a)pyrimidine; or a pharmaceutically acceptable acid addition or quaternary salt thereof.

3. A compound of the formula:

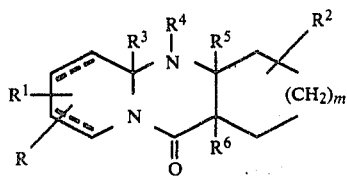

wherein
R is hydrogen, hydroxy or $C_1$ to $C_4$ alkyl;
$R^1$ is hydrogen or $C_1$ to $C_4$ alkyl;
$R^2$ is hydrogen or $C_1$ to $C_4$ alkyl;
$R^3$ is hydrogen;
$R^4$ is hydrogen or $C_1$ to $C_4$ alkyl or $R^3$ and $R^4$ form a chemical bond;
$R^5$ is hydrogen;
$R^6$ is hydrogen or $R^5$ and $R^6$ form a chemical bond; and
m is 3 or 4;
or a pharmaceutically acceptable acid addition or quaternary salt thereof.

4. A compound of the formula:

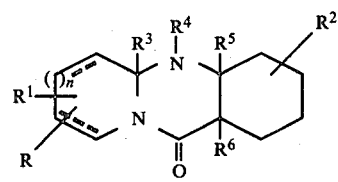

wherein
R is hydrogen or $C_1$ to $C_4$ alkyl;
$R^1$ is hydrogen or $C_1$ to $C_4$ alkyl;
$R^2$ is hydrogen or $C_1$ to $C_4$ alkyl;
$R^3$ is hydrogen;
$R^4$ is hydrogen or $C_1$ to $C_4$ alkyl or $R^3$ and $R^4$ form a chemical bond;
$R^5$ is hydrogen;
$R^6$ is hydrogen or $R^5$ and $R^6$ form a chemical bond; and
n is 2; or a pharmaceutically acceptable acid addition or quaternary salt thereof.

5. The compound defined in claim 3 selected from the group consisting of:
2,3-pentamethylene-4-oxo-4H-pyrido(1,2-a)pyrimidine;
2,3-pentamethylene-6-methyl-4-oxo-4H-pyrido(1,2-a)pyrimidine;
2,3-pentamethylene-9-hydroxy-4-oxo-4H-pyrido(1,2-a)pyrimidine;
2,3-hexamethylene-6-methyl-4-oxo-4H-pyrido(1,2-a)pyrimidine;
2,3-hexamethylene-4-oxo-4H-pyrido(1,2-a)pyrimidine;
2,3-hexamethylene-9-hydroxy-4-oxo-4H-pyrido(1,2-a)pyrimidine;
2,3-pentamethylene-4-oxo-6,7,8,9-tetrahydro-4H-pyrido(1,2-a)pyrimidine;
2,3-hexamethylene-4-oxo-6,7,8,9-tetrahydro-4H-pyrido(1,2-a)pyrimidine;
2,3-pentamethylene-6-methyl-4-oxo-6,7,8,9-tetrahydro-4H-pyrido-(1,2-a)pyrimidine; and
2,3-hexamethylene-6-methyl-4-oxo-6,7,8,9-tetrahydro-4H-pyrido-(1,2-a)pyrimidine; or a pharmaceutically acceptable acid addition or quaternary salt thereof.

6. The compound defined in claim 4 selected from the group consisting of:
2,3-cis-(tetramethylene)-4-oxo-2,3,4,6,7,8,9,10-octahydro-azepino-(1,2-a)pyrimidine;
2,3-cis-(tetramethylene)-8-t-butyl-4-oxo-2,3,4,6,7,8,9,10-octahydro-azepino(1,2-a)pyrimidine;
2,3-cis-(tetramethylene)-4-oxo-1,2,3,4,6,7,8,9,10,10a-decahydro-azepino(1,2-a)pyrimidine; and
2,3-cis-(tetramethylene)-8-t-butyl-4-oxo-1,2,3,4,6,7,8,9,10,10a-decahydro-azepino(1,2-a)pyrimidine; or a pharmaceutically acceptable acid addition or quaternary salt thereof.

7. A compound selected from the group consisting of:
7-methyl-2,3-trimethylene-4-oxo-4H-pyrido(1,2-a)pyrimidine;
6,8-dimethyl-2,3-trimethylene-4-oxo-4H-pyrido(1,2-a)pyrimidine;
6-methyl-2,3-tetramethylene-4-oxo-4H-pyrido(1,2-a)pyrimidine;
2,3-pentamethylene-4-oxo-4H-pyrido(1,2-a)pyrimidine; and
2,3-hexamethylene-4-oxo-4H-pyrido(1,2-a)pyrimidine; or a pharmaceutically acceptable acid addition or quaternary salt thereof.

8. 6,8-Diemthyl-2,3-trimethylene-4-oxo-4H-pyrido(1,2-a)pyrimidine or a pharmaceutically effective acid-addition or quaternary salt thereof as defined in claim 1.

9. 6-Methyl-2,3-tetramethylene-4-oxo-4H-pyrido(1,2-a)pyrimidine or a pharmaceutically effective acid-addition or quaternary salt thereof as defined in claim 1.

* * * * *